(12) United States Patent
Yasuhara et al.

(10) Patent No.: US 7,880,552 B2
(45) Date of Patent: *Feb. 1, 2011

(54) CONTROL SYSTEM FOR WALKING ASSIST DEVICE

(75) Inventors: Ken Yasuhara, Wako (JP); Yoshihiro Miyake, Yokohama (JP)

(73) Assignee: Honda Giken Kogyo Kabushiki Kaisha, Tokyo (JP)

( * ) Notice: Subject to any disclaimer, the term of this patent is extended or adjusted under 35 U.S.C. 154(b) by 1835 days.

This patent is subject to a terminal disclaimer.

(21) Appl. No.: 10/515,557

(22) PCT Filed: Aug. 5, 2003

(86) PCT No.: PCT/JP03/09918

§ 371 (c)(1), (2), (4) Date: Nov. 23, 2004

(87) PCT Pub. No.: WO2004/017890

PCT Pub. Date: Mar. 4, 2004

(65) Prior Publication Data

US 2005/0177080 A1 Aug. 11, 2005

(30) Foreign Application Priority Data

Aug. 21, 2002 (JP) .............................. 2002-240699

(51) Int. Cl.
*A61F 2/72* (2006.01)
(52) U.S. Cl. ........................... 331/65; 600/595; 623/25; 623/30
(58) Field of Classification Search .................... 331/65, 331/2; 623/25, 30; 602/16; 600/595; 135/67; 482/66; 601/5, 33
See application file for complete search history.

(56) References Cited

U.S. PATENT DOCUMENTS

2003/0023192 A1* 1/2003 Foxlin ........................ 600/595

(Continued)

FOREIGN PATENT DOCUMENTS

GB 2 278 041 11/1994

(Continued)

OTHER PUBLICATIONS

WO 95/01141, Constant Torque Range-of-Motion Splint, Publication Date: Jan. 12, 1995.

*Primary Examiner*—Joseph Chang
(74) *Attorney, Agent, or Firm*—Rankin, Hill & Clark LLP

(57) ABSTRACT

A system capable of controlling an autonomous walking assist rhythm, while following changes in a walking rhythm of a walker at the same time. A control system 100 in accordance with the present invention generates a first oscillator x that tugs and is tugged by a walking oscillator (hip joint angular velocity) $\phi_H'$ such that an intrinsic angular velocity is reflected. Then, a new intrinsic angular velocity $\omega_m$ is determined on the basis of the difference between a first phase difference $\theta_{HM}$ between the first oscillator x and the walking oscillator $\phi_H'$ and a desired phase difference $\theta_d$. Furthermore, a second oscillator y is generated that tugs and is tugged by the walking oscillator $\phi_H'$ such that the intrinsic angular velocity $\omega_m$ is reflected, and has a second phase difference $\theta_{hm}$, which is closer to the desired phase difference $\theta_d$ than the first phase difference $\theta_{HM}$ is, with respect to the walking oscillator $\phi_H'$. Then, based on the second oscillator y and the walking oscillator (hip joint angle) $\phi_H$, a walking assist oscillator (torque imparted to the walker by a walking assist unit 200) T is generated.

29 Claims, 10 Drawing Sheets

U.S. PATENT DOCUMENTS

2009/0131839 A1 * 5/2009 Yasuhara .................. 601/5

FOREIGN PATENT DOCUMENTS

| | | |
|---|---|---|
| JP | 58-163384 | 9/1983 |
| JP | 07-163607 | 6/1995 |
| JP | 08-278786 | 10/1996 |
| JP | 8-511975 | 12/1996 |
| JP | 2000-107213 | 4/2000 |
| JP | 2000-166997 | 8/2000 |
| JP | 2002-301124 | 10/2002 |
| JP | 2003-079684 | 3/2003 |
| JP | 2003-116893 | 4/2003 |
| JP | 2003-135543 | 5/2003 |
| JP | 2003-220102 | 8/2003 |
| WO | 94/09727 | 5/1994 |

* cited by examiner

CONTROL SYSTEM FOR WALKING ASSIST DEVICE

TECHNICAL FIELD

The present invention relates to a control system for a walking assist device.

BACKGROUND ART

There has been known a device adapted to assist a walker with his/her walking by imparting torques about leg joints (hip joints, knee joints, and foot joints) to the walker.

In the walking assist device, if a walking assist rhythm (a rhythm for imparting torque to a walker) is programmed beforehand, then the walker is forced to follow the walking rhythm based on the programmed walking assist rhythm. Therefore, if the walking assist rhythm is slow, then the walker has to walk slowly even if the walker wishes to walk faster. Conversely, if the walking assist rhythm is fast, then the walker has to walk fast even if the walker wishes to walk slowly. Hence, the walker is very likely to develop uncomfortableness, feeling that the walker is forced to walk in a manner against his/her will.

A walking assist rhythm arranged to fully follow a walking rhythm of a walker enables the walker to walk at a walking rhythm based on his/her own will.

In other words, if the walking assist rhythm is controlled to be faster in response to a change in the movement of legs when the walker moves his/her legs faster, speeding up the walking rhythm, then the walker will be able to walk faster as he/she intends to. Similarly, if the walking assist rhythm is controlled to be slower in response to a change in the movement of the legs when the walker moves his/her legs slowly, slowing down the walking rhythm, then the walker will be able to walk slowly as he/she intends to.

On the other hand, it is important for a walker wearing the walking assist device to feel that his/her walking is assisted since he/she is using the walking assist device. Hence, in walking assistance fully led by a walker, the walker may feel uncomfortable with the walk using the walking assist device due to such feeling of not being assisted, even if the walker can walk at an intended rhythm.

If a walking rhythm generated by a walker himself/herself suddenly changes or if the walking rhythm is unnatural from normal walk, then the walking based on the walking rhythm is furthered, possibly leading to an increase in burden to the mind and body of the walker.

Accordingly, the present invention is intended to achieve a solution by providing a system capable of controlling an autonomous walking assist rhythm, while following changes in a walking rhythm of a walker at the same time.

DISCLOSURE OF INVENTION

A control system for a walking assist device in accordance with the present invention to solve the aforesaid problem is characterized by comprising a walking oscillator measuring means for measuring a walking oscillator of a walker whose walk is assisted by a walking assist device, a first oscillator generating means for generating a first oscillator that tugs and is tugged by the walking oscillator measured by the walking oscillator measuring means such that an intrinsic angular velocity is reflected, a determining means for determining a new intrinsic angular velocity on the basis of a difference between a first phase difference between the first oscillator and the walking oscillator and a desired phase difference, a second oscillator generating means for generating a second oscillator that tugs and is tugged by the walking oscillator measured by the walking oscillator measuring means such that the intrinsic angular velocity determined by the determining means is reflected, and has a second phase difference, which is closer to the desired phase difference than the first phase difference is, with respect to the walking oscillator, and a walking assist oscillator generating means for generating a walking assist oscillator of the walking assist device on the basis of the second oscillator and the walking oscillator measured by the walking oscillator measuring means.

According to the present invention, it is possible to generate a oscillator having a proper phase difference from the viewpoint of walking assistance with respect to a walking oscillator in which a walking rhythm is reflected, and then a walking assist oscillator is generated on the basis of the oscillator, thereby allowing a walking assist rhythm to be optimized.

The "oscillator" used in the present invention means a realistic or virtual parameter that vibrates (temporally changes) at a certain rhythm (angular velocity). For example, the "walking oscillator" means a leg joint angle or a leg joint angular velocity or the like of a walker that vibrates at a rhythm in which a walking rhythm is reflected. The "walking assist oscillator" means an imparted torque or the like around leg joints applied to the walker that vibrates with a rhythm in which a walking assist rhythm is reflected.

More specifically, first, ① "the first oscillator" that tugs and is tugged by a walking oscillator such that "the intrinsic angular velocity" is reflected is generated. The first oscillator vibrates with an autonomous rhythm in which "the intrinsic angular velocity" is reflected while harmonizing with the rhythm of the walking oscillator due to the "mutual tugging" effect.

However, although the first oscillator harmonizes with the rhythm of the walking oscillator, the first phase difference relative to the walking oscillator is not necessarily a phase difference appropriate for assisting walk. Hence, if a walking assist oscillator is determined on the basis of the first oscillator, then a phase difference (~a first phase difference) inappropriate for assisting walk may be generated between a walking rhythm and a walking assisting rhythm, leading to inappropriate walking with the walking assistance. Accordingly, it is necessary to generate a new oscillator having a phase difference appropriate for walking assistance relative to the walking oscillator on the basis of the first oscillator.

Hence, ② a new "intrinsic angular velocity" is determined, and then "a second oscillator" is generated that tugs and is tugged by the walking oscillator such that the intrinsic angular velocity is reflected, and has "a second phase difference," which is closer to "a desired phase difference" than the first phase difference is, with respect to the walking oscillator.

The rhythm of the second oscillator has a phase difference (~a second phase difference) that is "a desired phase difference" or one close thereto relative to a walking rhythm (~rhythm of the walking oscillator). Thus, if the walking assist oscillator is determined on the basis of the second oscillator, then the phase difference between the walking rhythm and the walking assist rhythm approaches to the desired phase difference.

Then, ③ a walking assist oscillator is generated on the basis of the second oscillator and the walking oscillator. This generates the walking assist oscillator so as to realize a walking rhythm and the desired phase difference. Furthermore, the walk of the walker can be assisted at a rhythm based on a walking condition reflected in the walking oscillator and the walking rhythm.

Accordingly, the present invention makes it possible to achieve a walking assist rhythm that ①follows changes in the walking rhythm (~walking oscillator rhythm) of a walker, while ②maintaining autonomy that has the walking rhythm and "a desired phase difference," and ③ achieving smooth walking assistance according to a walking condition of the walker.

As described above, a walking assist rhythm harmonizes with a change in a walking rhythm when the walking rhythm changes, and the walking rhythm harmonizes with the walking assist rhythm, thus allowing the walker (human body) and a walking assist device (machine) to harmonize with each other (mutual concession). This arrangement makes it possible to achieve appropriate walking assistance, while allowing a walker to reasonably feel that his/her walk is being assisted by the walking assist device. Moreover, even if a walking rhythm suddenly changes, the walking assist rhythm does not fully follow the sudden change, making it possible to avoid furthering walking assistance and walking that cause burden to the mind and body of the walker.

The present invention is characterized by being further equipped with a walking condition determining means for determining the walking condition of the walker on the basis of a walking oscillator measured by the walking oscillator measuring means, and a desired phase difference determining means for determining a desired phase difference on the basis of the walking condition of the walker determined by the walking condition determining means.

The present invention is characterized by being further equipped with a physiological parameter measuring means for measuring physiological parameters indicating a physiological condition of a walker, a walking condition determining means for determining the walking condition of the walker on the basis of the physiological parameters measured by the physiological parameter measuring means, and a desired phase difference determining means for determining a desired phase difference on the basis of a walking condition of the walker determined by the walking condition determining means.

According to the present invention, it is possible to achieve walk with proper walking assistance responsive to changes in a walking condition by bringing a phase difference between a walking rhythm and a walking assist rhythm close to a desired phase difference that changes with the walking condition of the walker.

The present invention is characterized in that the walking condition determining means determines whether a walking condition of a walker is a flat walk condition, an ascending walk condition, or a descending walk condition, and the desired phase difference determining means basically determines a desired phase difference to be 0 for the flat walk condition, – for the ascending walk condition, and + for the descending walk condition.

According to the present invention, when the desired phase difference is determined to be +, the walking rhythm and the walking assist rhythm will have a phase difference of the determined value (>0) or a phase difference close thereto, enabling the walker to walk while leading the walking assist device. Conversely, when the desired phase difference is determined to be –, the walking rhythm and the walking assist rhythm will have a phase difference of the determined value (<0) or a phase difference close thereto, enabling the walker to walk while being led by the walking assist device.

Thus, the walker can walk by leading the walking assist device in the descending walk condition wherein burden is relatively small, while by being led by the walking assist device in the ascending walk condition wherein burden is relatively large. The desired phase difference can be changed according to walker's intention or other factors rather than being fixed to 0, + or – according to a walking condition.

Furthermore, the present invention is characterized in that the walking condition determining means determines the speed of walk as a walking condition, and the desired phase difference determining means basically determines a desired phase difference to be – if the walk is fast, or + if the walk is slow.

The present invention enables a walker to walk by leading the walking assist device for "slow walk" in which burden is relatively small, while by being led by the walking assist device for "fast walk" in which burden is relatively large.

The present invention is characterized by comprising a physiological parameter measuring means for measuring physiological parameters indicating a physiological condition of a walker, a physiological condition determining means for determining the physiological condition of the walker on the basis of the physiological parameters measured by the physiological parameter measuring means, and a desired phase difference determining means for determining a desired phase difference on the basis of a physiological condition of the walker determined by the physiological condition determining means.

According to the present invention, it is possible to achieve walk with proper walking assistance responsive to changes in a physiological condition by bringing a phase difference between a walking rhythm and a walking assist rhythm close to a desired phase difference that changes with the physiological condition of the walker.

The present invention is characterized in that the physiological condition determining means determines fatigue of a walker as a physiological condition of the walker, and basically determines a desired phase difference to be + if the fatigue of the walker is small, or – if the fatigue of the walker is large.

The present invention enables a walker to walk by leading the walking assist device if his/her fatigue is small, or by being led by the walking assist device if his/her fatigue is large.

Furthermore, according to the present invention, the first oscillator generating means generates a plurality of first oscillators corresponding to the motions of a plurality of virtual objects such that correlation among the plurality of the objects is reflected, and the second oscillator generating means generates a plurality of second oscillators corresponding to the motions of the plurality of virtual objects such that correlation among the plurality of the objects is reflected.

The present invention makes it possible to generate the first and second oscillators so that walking assist oscillators can be generated to further fit actual walk of a walker by adjusting an intensity level of correlation among virtual plural objects.

More specifically, if, for example, right and left legs or a plurality of joints of the same leg are assumed as virtual plural objects, then "the first oscillator" and "the second oscillator" and furthermore "a walking assist oscillator" are generated such that a qualitative correlation between the right and left legs, such as alternate, longitudinal motion, and qualitative correlation or the like among joints of the same leg, such as periods, phase differences, etc. of leg motions about hip joints and leg motions about knee joints, are reflected. With this arrangement, a generated walking assist rhythm based on a generated walking assist oscillator can be adjusted to a rhythm appropriate for a walker on the basis of the qualitative correlation.

The present invention is characterized by comprising a walking condition determining means for determining a walking condition of a walker on the basis of a walking oscillator measured by a walking oscillator measuring means and a first correlation adjusting means for adjusting a correlation among a plurality of virtual objects related to generation of first and second oscillators on the basis of a walking condition of the walker determined by the walking condition determining means.

Furthermore, the present invention is characterized by comprising a physiological parameter measuring means for measuring physiological parameters indicating a physiological condition of a walker, a walking condition determining means for determining the walking condition of the walker on the basis of the physiological parameters measured by the physiological parameter measuring means, and a first correlation adjusting means for adjusting a correlation among a plurality of virtual objects related to the generation of the first and second oscillators on the basis of the walking condition of the walker determined by the walking condition determining means.

According to the present invention, a walking assist rhythm can be properly adjusted on the basis of a qualitative correlation of right and left legs or the like assumed as the plurality of virtual objects, as described above, and walking assistance at an optimum rhythm based on a walking condition can be achieved in real time such that a circumstance in which the qualitative correlation changes as "the walking condition" of the walker changes is reflected.

The present invention is characterized by comprising a physiological parameter measuring means for measuring physiological parameters indicating a physiological condition of a walker, a physiological condition determining means for determining the physiological condition of the walker on the basis of the physiological parameters measured by the physiological parameter measuring means, and a first correlation adjusting means for adjusting a correlation among a plurality of virtual objects related to the generation of the first and second oscillators on the basis of the physiological condition of the walker determined by the physiological condition determining means.

According to the present invention, a walking assist rhythm can be properly adjusted on the basis of a qualitative correlation of right and left legs or the like assumed as the plurality of virtual objects, as described above, and walking assistance at an optimum rhythm based on a physiological condition can be achieved in real time such that a circumstance in which the qualitative correlation changes as "the physiological condition" of the walker changes is reflected.

The present invention is characterized in that a determining means determines an intrinsic angular velocity for bringing a second phase difference between a second oscillator and a walking oscillator closer to a desired phase difference than a first phase difference between a first oscillator and a walking oscillator is, according to an internal model representing a phase relationship between a virtual walking oscillator and a virtual walking assist oscillator.

The present invention is characterized in that a determining means is provided with a correlation factor determining means for determining correlation factors of a virtual walking oscillator and a virtual walking assist oscillator such that a second phase difference of the virtual walking oscillator and the virtual walking assist oscillator approaches to a first phase difference according to an internal model, a first angular velocity determining means for determining an angular velocity of the virtual walking oscillator on the basis of the correlation factors, and a second angular velocity determining means for determining an angular velocity of the virtual walking assist oscillator as an intrinsic angular velocity related to the generation of the second oscillator such that the second phase difference approaches to a desired phase difference on the basis of the angular velocity of the virtual walking oscillator.

According to the present invention, a phase difference (~a second phase difference) between a virtual walking rhythm and a virtual walking assist rhythm is brought closer to "a desired phase difference" than a first phase difference is. This makes it possible to bring a phase difference between an actual walking assist rhythm and an actual walking rhythm close to "the desired phase difference" suited to the walking provided with walking assistance.

The present invention is characterized in that the walking assist oscillator generating means generates a walking assist oscillator corresponding to behaviors of a plurality of virtual neural elements such that a correlation among the plurality of virtual neural elements is reflected.

According to the present invention, it is possible to achieve walking assistance that is more suitable to actual walking of a walker by adjusting the intensity of correlation among a plurality of virtual neural elements.

Furthermore, the present invention is characterized by comprising a walking condition determining means for determining a walking condition of a walker on the basis of a walking oscillator measured by a walking oscillator measuring means, and a second correlation adjusting means for adjusting a correlation among a plurality of virtual neural elements related to the generation of a walking assist oscillator on the basis of the walking condition of the walker determined by the walking condition determining means.

Furthermore, the present invention is characterized by comprising a physiological parameter measuring means for measuring physiological parameters indicating a physiological condition of a walker, a walking condition determining means for determining the walking condition of the walker on the basis of the physiological parameters measured by the physiological parameter measuring means, and a second correlation adjusting means for adjusting a correlation among a plurality of virtual neural elements related to the generation of the a walking assist oscillator on the basis of the walking condition of the walker determined by the walking condition determining means.

According to the present invention, a walking assist rhythm can be properly adjusted by adjusting the intensity of correlation among the plurality of virtual neural elements, as described above, and walking assistance at an optimum rhythm based on a walking condition can be achieved in real time such that a circumstance in which the intensity of correlation changes as "the walking condition" of the walker changes is reflected.

The present invention is characterized by comprising a physiological parameter measuring means for measuring physiological parameters indicating a physiological condition of a walker, a physiological condition determining means for determining the physiological condition of the walker on the basis of the physiological parameters measured by the physiological parameter measuring means, and a second correlation adjusting means for adjusting a correlation among a plurality of virtual neural elements related to the generation of the walking assist oscillator on the basis of the walking condition of the walker determined by the walking condition determining means.

According to the present invention, a walking assist rhythm can be properly adjusted by adjusting the intensity of correlation among the plurality of virtual neural elements, as described above, and walking assistance at an optimum rhythm based on a physiological condition can be achieved in real time such that a circumstance in which the intensity of correlation changes as "the physiological condition" of the walker changes is reflected.

The present invention is characterized by comprising a storing means for storing a correspondence relationship between a walking condition and a tracing pattern drawn in an n-dimensional space by an n number of walking oscillators, wherein the walking condition determining means determines a walking condition on the basis of the correspondence relationship stored by the storing means and the tracing pattern drawn in the n-dimensional space by the n number of walking oscillators measured by the walking oscillator measuring means.

According to the present invention, a walking condition can be determined with high accuracy on the basis of a certain relationship (found by the inventors of the application concerned) between a walking condition and a trace drawn by the n number of walking oscillators in the n-dimensional space.

Furthermore, the present invention is characterized in that the first and second oscillator generating means generate the first and second oscillators according to a nonlinear oscillator model represented by the Van der Pol equation that includes a walking oscillator measured by the walking oscillator measuring means.

According to the present invention, mutual tugging between walking oscillators and the first and second oscillators can be adjusted by adjusting a term included in the Van der Pol equation.

Furthermore, the present invention is characterized in that the walking oscillator measuring means measures the first oscillators, the second oscillators, and at least one of various oscillators including a joint angle and angular velocity of a walker that periodically changes at a rhythm corresponding to a walking rhythm, as a walking oscillator for generating a walking assist oscillator.

According to the present invention, the first oscillators, the second oscillators, and the walking assist oscillators can be generated on the basis of a joint angular velocity and angles (walking oscillators) that vibrate such that an actual walking rhythm is accurately reflected.

The present invention is characterized in that the walking assist oscillator generating means generates, as a walking assist oscillator, a torque about a leg joint imparted to a walker, or a oscillator that periodically changes in a form perceivable by a walker in response to a torque and a change in torque.

According to the present invention, a torque or the like about a leg joint can be imparted to a walker at a rhythm harmonized with a walking rhythm of the walker with a desired phase difference.

The present invention is characterized in that the walking oscillator measuring means measures, as a walking oscillator for determining a walking condition, at least one of a leg joint angle, a leg joint angular velocity, a leg joint angular acceleration, and the position of a part of a leg of a walker.

According to the present invention, a walking condition is determined on the basis of a leg joint angular velocity or the like closely related to the walking condition, permitting improved accuracy of the determination to be achieved.

BEST MODE FOR CARRYING OUT THE INVENTION

An embodiment of the control system for a walking assist device in accordance with the present invention will be explained in conjunction with the accompanying drawings.

In the following explanation, apostrophes (') and double-apostrophes (") attached to variables (except for circled numerals) represent time-dependent one time differentiation and two time differentiation, respectively, of the variables. Subscripts L and R will be attached to parameters in order to distinguish left and right legs or the like of a walker. However, the subscripts L and R will be omitted, as appropriate, when there is no need to distinguish right and left.

Figure 1:
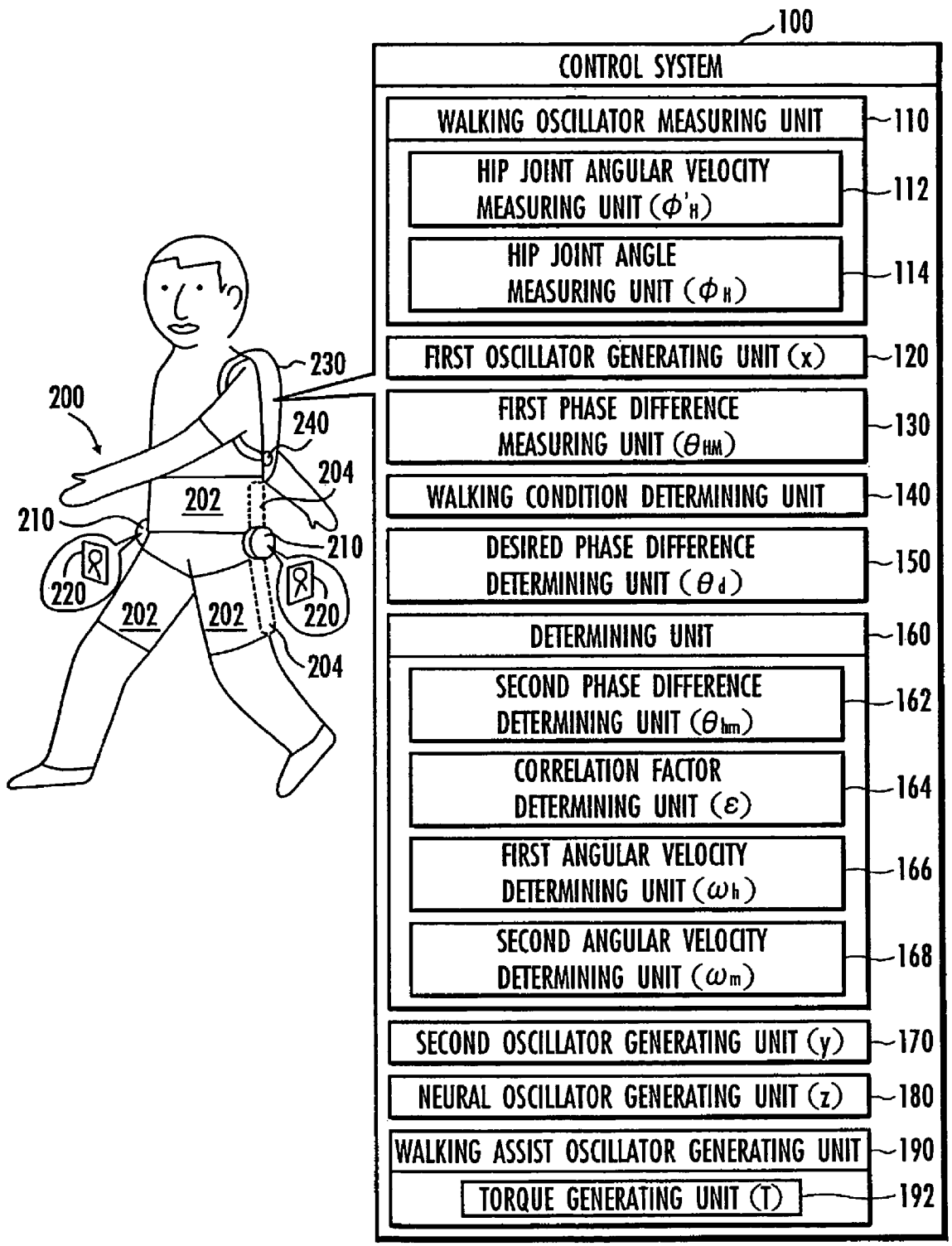
FIG. 1 is a constructional explanatory diagram of an embodiment of a control system in accordance with the present invention.

A walking assist device 200 to be controlled by a control system 100 shown in FIG. 1 is equipped with supporters 202 attached to the abdomen and right and left thighs of a walker, rigid members 204 made integral with the supporters 202, actuators 210 located on sides of the waist of the walker to impart torques about hip joints to the walker through the supporters 202 and the rigid members 204, angle sensors 220 that output signals based on the angles of the right and left hip joints, and a battery 240 built in a backpack 230 carried on the back of the walker to serve as a power source of the actuators 210, etc.

The control system 100 is constructed of a CPU (arithmetic processing unit), a ROM, a RAM or other types of memories (not shown) built in the backpack 230. The control unit 100 is further provided with a walking oscillator measuring unit 110, a first oscillator generating unit 120, a first phase difference measuring unit 130, a walking condition determining unit 140, a desired phase difference determining unit 150, a determining unit 160, a second oscillator generating unit 170, a neural oscillator generating unit 180, and a walking assist oscillator generating unit 190.

The walking oscillator measuring unit 110 includes a hip joint angular velocity measuring unit 112, and a hip joint angle measuring unit 114. The hip joint angular velocity measuring unit 112 measures a hip joint angular velocity $\phi_H'$ on the basis of an output of the angle sensor 220. The hip joint angle measuring unit 114 measures a hip joint angle $\phi_H$ on the basis of an output of the angle sensor 220.

The first oscillator generating unit 120 generates first oscillators (to be discussed later) x that tug with each other such that the hip joint angular velocity $\phi_H'$ that changes with an angular velocity $\omega_H$ measured by the hip joint angular velocity measuring unit 112 and an intrinsic angular velocity $\omega_M$ are reflected. The first oscillators x are generated according to a nonlinear oscillator model expressed by a Van der Pol equation, which will be discussed later.

The first phase difference measuring unit 130 measures a first phase difference $\theta_{HM}$ between the hip joint angular velocity $\phi_H'$ that changes with the angular velocity $\omega_H$ and the first oscillator x in which the intrinsic angular velocity $\omega_M$ included in the Van der Pol equation is reflected.

The walking condition determining unit 140 is equipped with a memory (not shown) storing a correspondence relationship between "a walking condition" and "a tracing pattern drawn in an n-dimensional space (plane)" by an n number of walking oscillators including the hip joint angular velocity $\phi_H'$. The walking condition determining unit 140 also determines a "walking condition" on the basis of the "correspondence relationship" stored in the memory and the "tracing pattern drawn in an n-dimensional space by the n number of walking oscillators" measured by the walking oscillator measuring unit 110.

The desired phase difference determining unit 150 determines a desired phase difference $\theta_d$ on the basis of a "walking condition" determined by the walking condition determining unit 140.

The determining unit 160 is equipped with a second phase difference determining unit 162, a correlation factor determining unit 164, a first angular velocity determining unit 166, and a second angular velocity determining unit 168.

The second phase difference measuring unit 162 determines a second phase difference $\theta_{hm}(=\theta_h-\theta_m)$ between a virtual walking oscillator $\theta_h$ and a virtual walking assist oscillator $\theta_m$ according to an "internal model" representing a phase relationship between the virtual walking oscillator (phase) $\theta_h$ and the virtual walking assist oscillator (phase) $\theta_m$.

The correlation factor determining unit 164 determines a correlation factor $\epsilon$ between the virtual walking oscillator $\theta_h$ and the virtual walking assist oscillator $\theta_m$ such that the second phase difference $\theta_{hm}(=\theta_h-\theta_m)$ approaches to a first phase difference $\theta_{HM}$.

The first angular velocity determining unit 166 determines an angular velocity $\omega_h$ of the virtual walking oscillator $\theta_h$ on the basis of the correlation factor $\epsilon$.

Based on the angular velocity $\omega_h$ of the virtual walking oscillator $\theta_h$, the second angular velocity determining unit 168 determines an angular velocity $\omega_m$ of the virtual walking assist oscillator $\theta_m$ such that the second phase difference $\theta_{hm}$ approaches to the desired phase difference $\theta_d$ determined by the desired phase difference determining unit 150.

The second oscillator generating unit 170 generates second oscillators (to be discussed later) y that tug with each other such that the hip joint angular velocity (the walking oscillator) $\phi_H'$ measured by the hip joint angular velocity measuring unit 112 and an angular velocity $\omega_m$ of the virtual walking assist oscillator $\theta_m$, determined by the second angular velocity determining unit 166 are reflected as an intrinsic angular velocity ($\omega_M$). The second oscillator y is generated according to a nonlinear oscillator model expressed by the Van der Pol equation, as in the case of the first oscillator x.

The neural oscillator generating unit 180 generates an output (neural oscillator) z of each neural element according to a neural oscillator model (to be discussed later) representing behaviors of a plurality of neural elements (neurons) related to walking on the basis of the second oscillator y and the hip joint angle (walking oscillator) $\phi_H$ measured by the hip joint angle measuring unit 114.

The walking assist oscillator generating unit 190 has a torque generating unit 192 that generates a torque (walking assist oscillator) T imparted to a walker by the walking assist device 200 on the basis of the output z of each neural element.

The function of the control system 100 of the walking assist device 200 will be explained in conjunction with FIG. 2 and FIG. 3.

Figure 2:
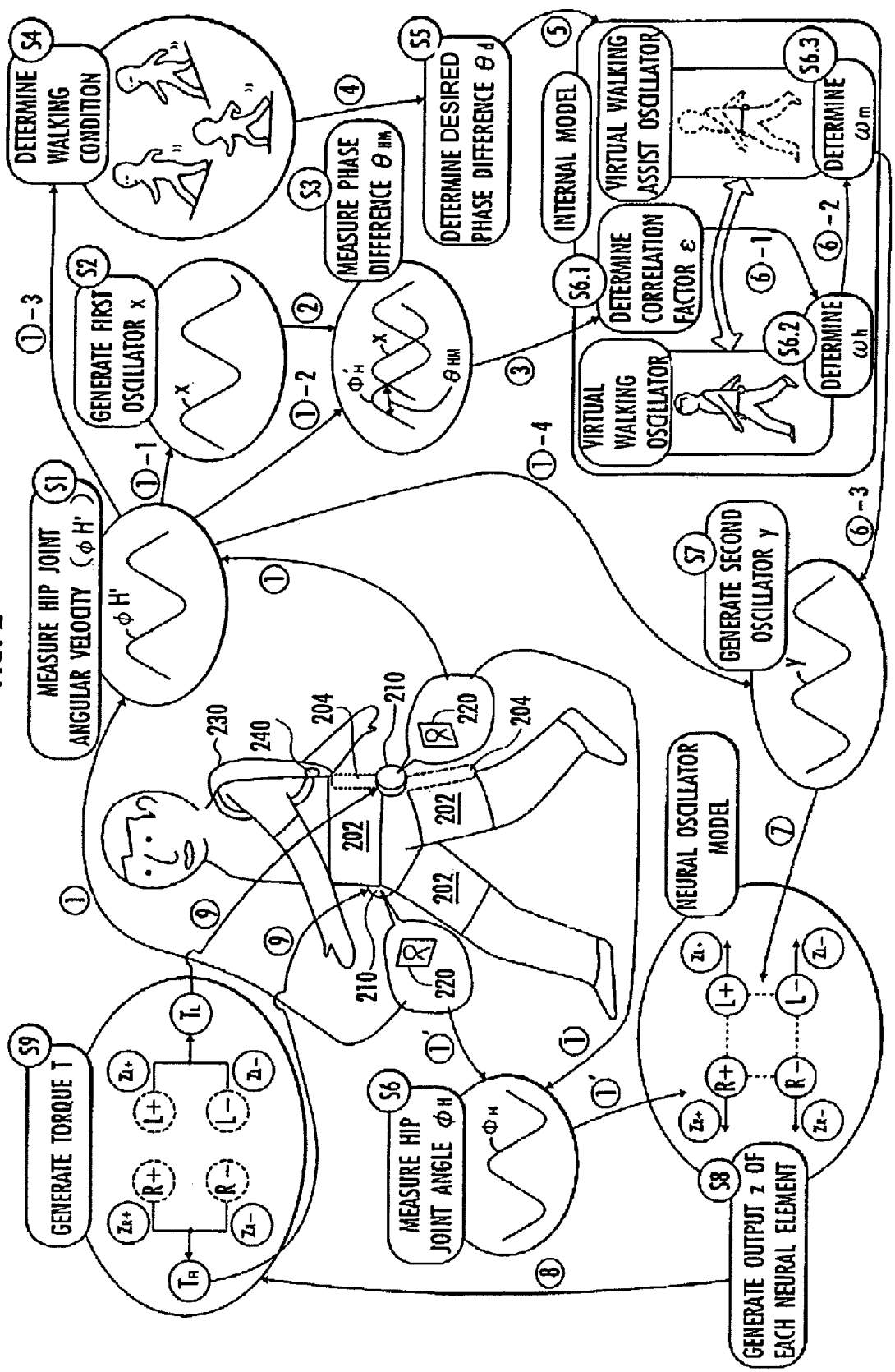
FIG. 2 is a functional explanatory diagram of the embodiment of the control system in accordance with the present invention.
Figure 3:
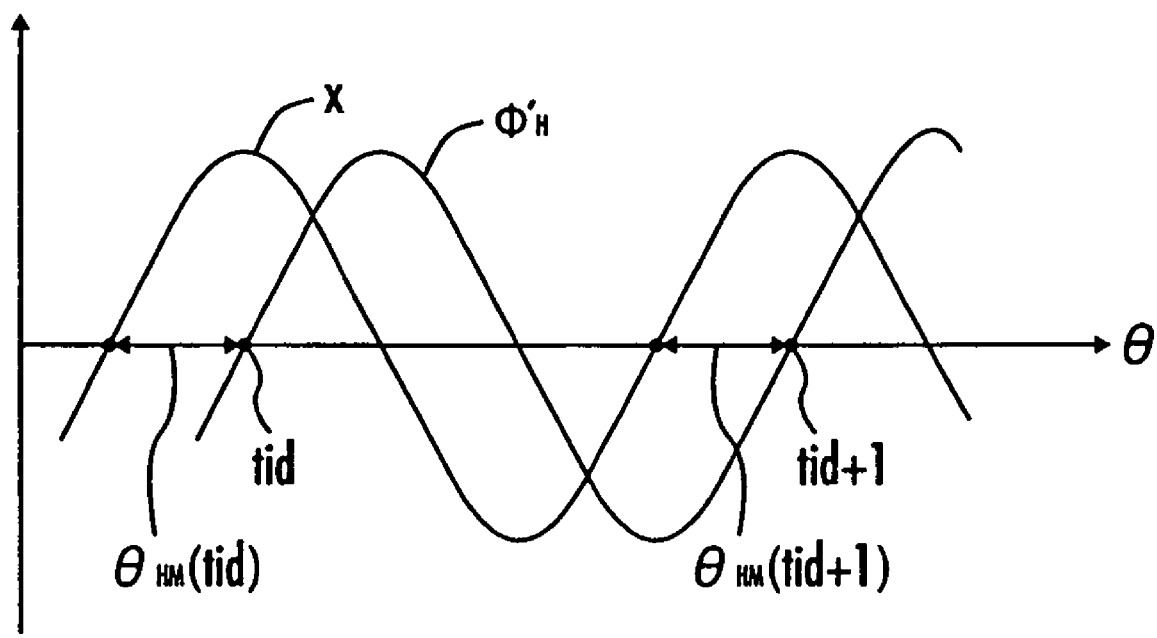
FIG. 3 is an explanatory diagram related to a correlation between two oscillators.

First, based on an output of an angle sensor 220 (refer to arrow ①  in FIG. 2), angular velocities $\phi_{HL}'$ and $\phi_{HR}'$ about left and right hip joints of the walker are measured by the hip joint angular velocity measuring unit 112 (s1 in FIG. 2).

Next, first oscillators $X_L$ and $X_R$ are determined (s2 in FIG. 2) by the first oscillator generating unit 120 on the basis of the hip joint angular velocities $\phi_{HL}'$ and $\phi_{HR}'$ (refer to arrow ①-1 in FIG. 2) according to the Van der Pol equation represented by expressions (1a) and (1b) given below.

$$x_L'' = \xi(1 - x_L^2)x_L' - \omega_{ML}^2 x_L + g(x_L - x_R) + c_1\phi_{HL}' \quad (1a)$$

$$x_R'' = \xi(1 - x_R^2)x_R' - \omega_{MR}^2 x_R + g(x_R - x_L) + c_1\phi_{HR}' \quad (1b)$$

where $\xi$ denotes a coefficient (>0) determined such that the first oscillator x and its time-dependent one differentiation x' draw a stable limit period on an x-x' plane. $\omega_M$ denotes an intrinsic angular velocity. g denotes a correlation factor of right/left leg. $c_1$ denotes a feedback coefficient. The intrinsic angular velocity $\omega_M$ may be arbitrarily set within a range in which it does not deviate significantly from an actual walking assist rhythm by the walking assist device 200.

The first oscillators $x_L$ and $x_R$ are determined by the Runge-Kutta method. The first oscillators $x_L$ and $x_R$ represent virtual walking assist rhythms related to the left and right legs, respectively. Because of the "mutual tugging", which is one of the properties of the Van der Pol equation, the first oscillators $x_L$ and $x_R$ have properties in which they vibrate with an autonomous rhythm in which the "intrinsic angular velocities" $\omega_{ML}$ and $\omega_{MR}$ are reflected, while harmonizing with the hip joint angular velocities (walking oscillators) $\phi_{HL}'$ and $\omega_{HR}'$ (refer to FIG. 3). The hip joint angular velocities (walking oscillators) $\phi_{HL}'$ and $\phi_{HR}'$ vibrate with a rhythm that is substantially equivalent to an actual walking rhythm (refer to FIG. 3.).

Subsequently, the phase difference measuring unit 130 determines (s3 in FIG. 2) first phase differences $\theta_{HML}(=\theta_{HL}-\theta_{ML})$, $\theta_{HMR}(=\theta_{HR}-\theta_{MR})$ between the hip joint angular velocities (walking oscillators) $\phi_{HL}'$ and $\phi_{HR}'$ (phases $\theta_{HL}$, $\theta_{HR}$/refer to arrow ①-2 in FIG. 2) and the first oscillators $x_L$ and $x_R$ (phases $\theta_{ML}$, $\theta_{MR}$/refer to arrow ② in FIG. 2). Specifically, as shown in FIG. 3, a phase difference $\theta_{HM}(=\theta_H-\theta_M)$ between a phase $\theta_H$ of the hip joint angular velocity $\phi_H'$ and a phase $\theta_M$ of the first oscillator x is determined on the basis of a time difference between a point at which $\phi_H'=0$ and $\phi_H''>0$ ( ... $t_{id}$, $t_{id}+1$, ... ) and a point at which x=0 and x'>0.

Furthermore, the walking condition determining unit 140 determines a walking condition (s4) on the basis of an n number (n =1, 2, ... ) of walking oscillators (refer to arrow ①-3 in FIG. 2) that include hip joint angular velocities $\phi_H'$ measured by the walking condition determining unit 110.

Specifically, first, the walking condition determining unit 140 reads, from a memory (not shown), a correspondence relationship between "walking condition" and "tracing patterns drawn in an n-dimensional space by an n number of walking oscillators." Then, the walking condition determining unit 140 determines a "walking condition" on the basis of the correspondence relationship and the tracing patterns drawn in the n-dimensional space by the n number of walking oscillators measured by the walking oscillator measuring unit 110.

As the walking oscillators for determining walking conditions, various parameters, such as the hip joint angle $\phi_H$, or the angles or angular velocities of knee joins, foot joints, shoulder joints or elbow joints, angular accelerations, the position of a part of a leg of a walker, or a landing noise, breath sound, or intended utterance of the walker, which vary with a rhythm associated with a walking rhythm may be measured by the walking oscillator measuring unit 110. Walking conditions of the walker determined by the walking condition determining unit 140 include "flat walk condition," "ascending walk condition," and "descending walk condition."

The desired phase difference determining unit 150 determines a desired phase difference $\theta_d$ (s5 in FIG. 2) on the basis of a "walking condition" (arrow ④ in FIG. 2) determined by the walking condition determining unit 140. More specifically, the desired phase difference determining unit 150 basically determines the desired phase difference $\theta_d$ to be 0 for the flat walk condition, for the ascending walk condition (e.g., −0.5 [rad] or less), and + for the descending walk condition (e.g., +0.3 [rad] or more).

If the first phase difference $\theta_{HM}$ measured by the phase difference measuring unit 130 remains constant for the past three walk periods, then a second phase difference $\theta_{hm}$ (=$\theta_h$−$\theta_m$) between a virtual walking oscillator $\theta_h$ and a virtual walking assist oscillator $\theta_m$ is determined according to "an internal model" represented by the following expressions (2a) and (2b) by the second phase difference determining unit 162.

$$\theta_h' = \omega_h + \epsilon \cdot \sin(\theta_m - \theta_h) \tag{2a}$$

$$\theta_m' = \omega_m + \epsilon \cdot \sin(\theta_h - \theta_m) \tag{2b}$$

where $\epsilon$ denotes correlation factors of the virtual walking oscillator $\theta_h$ and the walking assist oscillator $\theta_m$ in the internal model. $\omega_h$ denotes an intrinsic angular velocity of the virtual walking oscillator $\theta_h$, and $\omega_m$ denotes an intrinsic angular velocity of the virtual walking assist oscillator $\theta_m$.

Specifically, the second phase difference determining unit 162 determines the second phase difference $\theta_{hm}$ (=$\theta_h$−$\theta_m$) between the virtual walking oscillator $\theta_h$ and the virtual walking assist oscillator $\theta_m$ according to the following expression (3).

$$\theta_{hm} = \sin^{-1}[(\omega_h - \omega_m)/2\epsilon] \tag{3}$$

Subsequently, the correlation factor determining unit 164 determines the correlation factor $\epsilon$ (s6.1 in FIG. 2) so that a difference $\theta_{HM} - \theta_{hm}$ between the first phase difference $\theta_{HM}$ (refer to arrow ③ in FIG. 2) and the second phase difference $\theta_{hm}$ is minimized.

Specifically, the correlation factor $\epsilon$ is determined one after another at discrete time (..., $t_{id}$−1, $t_{id}$, $t_{id}$+1, ... /refer to FIG. 3) at which the hip joint angular velocity (walking oscillator) $\phi_H'$ becomes zero, according to the following expressions (4a) and (4b).

$$\varepsilon(t_{id} + 1) = \varepsilon(t_{id}) - \eta\{V_1(t_{id} + 1) - V_1(t_{id})\}/\{\varepsilon(t_{id}) - \varepsilon(t_{id} - 1)\} \tag{4a}$$

$$V_1(t_{id} + 1) \equiv (1/2)\{\theta_{HM}(t_{id} + 1) - \theta_{hm}(t_{id})\}^2 \tag{4b}$$

where $\eta$ denotes a coefficient representing stability of a potential $V_1$ for bringing the first phase difference $\theta_{HM}$ and the second phase difference $\theta_{hm}$ close to each other.

Then, based on the correlation factor $\epsilon$ (refer to arrow ④-1 in FIG. 2), the first angular velocity determining unit 166 determines, according to the following expressions (5a) and (5b), an intrinsic angular velocity $\omega_h$ of the virtual walking oscillator $\theta_h$ such that the difference of the first and second phase differences $\theta_{HM} - \theta_{hm}$ is minimized under a condition wherein the intrinsic angular velocity $\omega_m$ of the virtual walking assist oscillator $\theta_m$ remains constant without changing with time (s6.2 in FIG. 2).

$$\omega_{hL}(t_{idL}) = -\alpha \times \int dt \big([4\varepsilon(t_{idL})^2 - \{\omega_{hL}(t) - \omega_{mL}(t_{idL})\}^2\big]^{1/2} \times \tag{5a}$$
$$\sin[\sin^{-1}\{(\omega_{hL}(t) - \omega_{mL}(t_{idL} - 1))/2\varepsilon(t_{idL})\} - \theta_{HM}(t_{idL})])$$

$$\omega_{hR}(t_{idR}) = -\alpha \times \int dt \big([4\varepsilon(t_{idR})^2 - \{\omega_{hR}(t) - \omega_{mR}(t_{idR})\}^2\big]^{1/2} \times \tag{5b}$$
$$\sin[\sin^{-1}\{(\omega_{hR}(t) - \omega_{mR}(t_{idR} - 1))/2\varepsilon(t_{idR})\} - \theta_{HM}(t_{idR})])$$

where $\alpha$ denotes a coefficient representing stability of a system.

Subsequently, based on the intrinsic angular velocity $\omega_h$ of the virtual walking oscillator $\theta_h$ (refer to arrow ④-2 in FIG. 2), the intrinsic angular velocity $\omega_m$ of the virtual walking assist oscillator $\theta_m$ is determined by the second angular velocity determining unit 168 according to the following expressions (6a) and (6b) such that the second phase difference $\theta_{HM}$ approaches to the desired phase difference $\theta_d$ (refer to arrow ⑤ in FIG. 2) determined by the desired phase difference determining unit 150 (s6.3 in FIG. 2).

$$\omega_{mL}(t_{idL}) = \beta \int dt [4\varepsilon(t_{idL})^2 - \{\omega_{hL}(t_{idL}) - \omega_{mL}(t)\}^2] \times \tag{6a}$$
$$\sin[\sin^{-1}\{(\omega_{hL}(t_{idL}) - \omega_{mL}(t))/2\varepsilon(t_{idL})\} - \theta_d])$$

$$\omega_{mR}(t_{idR}) = \beta \int dt [4\varepsilon(t_{idR})^2 - \{\omega_{hR}(t_{idR}) - \omega_{mR}(t)\}^2] \times \tag{6b}$$
$$\sin[\sin^{-1}\{(\omega_{hR}(t_{idR}) - \omega_{mR}(t))/2\varepsilon(t_{idR})\} - \theta_d])$$

where $\beta$ denotes a coefficient representing stability of a system.

Next, second oscillators $y_L$ and $y_R$ are determined (s7 in FIG. 2) by the second oscillator generating unit 170 on the basis of the hip joint angular velocities $\phi_{HL}'$ and $\phi_{HR}'$ (refer to arrow ①-4 in FIG. 2) according to the Van der Pol equation represented by expressions (7a) and (7b) given below that include intrinsic angular velocities $\omega_{mL}$ and $\omega_{mR}$ determined by the second angular velocity determining unit 168 (refer to arrow ④-3 in FIG. 2).

$$y_L'' = \xi(1 - y_L^2)y_L' - \omega_{mL}y_L + g(y_L - y_R) + c_1\phi_{HL}' \tag{7a}$$

$$y_R'' = \xi(1 - y_R^2)y_R' - \omega_{mR}y_R + g(y_R - y_L) + c_1\phi_{HR}' \tag{7b}$$

The second oscillators $y_L$ and $y_R$ are determined by the Runge-Kutta method, as in the case of the first oscillators $x_L$ and $x_R$. The second oscillators $y_L$ and $y_R$ represent virtual walking assist rhythms related to the left and right legs, respectively. Because of the "mutual tugging", which is one of the properties of the Van der Pol equation, the second oscillators $y_L$ and $y_R$ have properties in which they vibrate with an autonomous rhythm in which the "intrinsic angular velocities" $\omega_{mL}$ and $\omega_{mR}$ are reflected, while harmonizing with the rhythms of the hip joint angular velocities (walking oscillators) $\phi_{HL}'$ and $\phi_{HR}'$ (refer to FIG. 3).

Subsequently, a neural oscillator z is generated by the neural oscillator generating unit 180 (s8 in FIG. 2) according to a "neural oscillator model" on the basis of the second oscillators $y_L$ and $y_R$ (refer to arrow ⑦ in FIG. 2) and the left and right hip joint angles $\phi_L$ and $\phi_R$ (refer to arrow ①' in FIG. 2) measured by the hip joint angle measuring unit 114. The left and right hip joint angles $\phi_L$ and $\phi_R$ of the walker are measured by the hip joint angle measuring unit 114 in parallel to the measurement of the hip joint angular velocity $\phi_H'$ by the hip joint angular velocity measuring unit 112 (s1' in FIG. 2).

Specifically, outputs $z_{L+}$ and $z_{L-}$ of neural elements $L_+$ and $L_-$ that govern the motions of the left thigh in a bending direction (to the front) and a stretching direction (to the rear) and outputs $z_{R+}$ and $z_{R-}$ of neural elements $R_+$ and $R_-$ that govern the motions of the right thigh in the bending direction and the stretching direction are determined according to the following expressions (8a) through (8f).

$$\tau_{L+}u'_{L+} = -u_{L+} + w_{L+/L-}\, z_{L-} + w_{L+/R+}\, z_{R+} - \lambda v_{L+} + k_+\, \phi_R - c y_R \quad (8a)$$

$$\tau_{L-}u'_{L-} = -u_{L-} + w_{L-/L+}\, z_{L+} + w_{L-/R-}\, z_{R-} - \lambda v_{L-} - k_-\, \phi_R + c y_L \quad (8b)$$

$$\tau_{R+}u'_{R+} = -u_{R+} + w_{R+/L+}\, z_{L+} + w_{R+/R-}\, z_{R-} - \lambda v_{R+} + k_+\, \phi_L + c y_L \quad (8c)$$

$$\tau_{R-}u'_{R-} = -u_{R-} + w_{R-/L-}\, z_{L-} + w_{R-/R+}\, z_{R+} - \lambda v_{R-} + k_-\, \phi_R - c y_R \quad (8d)$$

$$\sigma_i v'_i = -v_i + z_i \quad (i = L_+, L_-, R_+, R_-) \quad (8e)$$

$$z_i = \max(0, u_i) \quad (8f)$$

where $u_i$ denotes a condition variable associated with a change in membrane potential of a neural element i, $v_i$ denotes a self inhibitor in which adaptation effect of the neural element i is reflected, $\tau_i$ and $\sigma_i$ are time constants of the condition variable $u_i$ and the self inhibitor $v_i$, $w_{i/j}$ (<0) denotes an association constant of the neural elements i and j, $\lambda$ denotes a habituation coefficient, $k_+$ and $k_-$ denote feedback coefficients, and c denotes a bias coefficient.

Next, torques about hip joints (walking assist oscillators) $T_L$ and $T_R$ imparted to the walker by the right and left actuators 220 are generated (s9 in FIG. 2) by the torque generating unit 192 on the basis of an output $y_i$ of the neural element i (refer to arrow ⑧ in FIG. 2) according to expressions (9a) and (9b) given below.

$$T_L = p_+ z_{L+} - p_- z_{L-} \quad (9a)$$

$$T_R = -p_+ z_{R+} + p_- z_{R-} \quad (9b)$$

where $p_+$ and $p_-$ denote activation coefficients.

Electric power based on the generated torques $T_L$ and $T_R$ is supplied from the battery 230 to the right and left actuators 210, so that the torques $T_L$ and $T_R$ are imparted to the walker through the actuators 210 (refer to arrow ⑨ in FIG. 2).

Thereafter, the above processing (s1 through s9 in FIG. 2) is repeated, causing the walker to walk with the walking assistance by the walking assist device 200.

According to the control system 100, it is possible to generate a second oscillator y having a proper phase difference (~desired phase difference $\theta_d$) from the viewpoint of walking assistance with respect to the hip joint angular velocity (walking oscillator) $\phi_H'$ in which a walking rhythm is reflected, and then the torque (walking assist oscillator) T is generated on the basis of the second oscillator y, thereby allowing a walking assist rhythm to be optimized.

To be more specific, first, (1) a first oscillator x that tugs and is tugged by the hip joint angular velocity (walking oscillator) $\phi_H'$ in which the intrinsic angular velocity $\omega_M$ is reflected is generated (s2 in FIG. 2). The first oscillator x vibrates with an autonomous rhythm in which the intrinsic angular velocity $\omega_M$ is reflected, while harmonizing with the rhythm of the hip joint angular velocity (walking oscillator) $\phi_H'$ due to the "mutual tugging" effect.

However, although the first oscillator x harmonizes with the rhythm (~walking rhythm) of the hip joint angular velocity (the walking oscillator) $\phi_H'$, the first phase difference $\theta_{HM}$ relative to the hip joint angular velocity $\phi_H'$ is not necessarily close to the desired phase difference $\theta_d$ appropriate for assisting walk. Hence, if the torque (walking assist oscillator) T is determined on the basis of the first oscillator x, then a phase difference (~a first phase difference $\theta_{HM}$) inappropriate for assisting walk may be generated between a walking rhythm and a walking assisting rhythm, leading to inappropriate walking with the walking assistance. Accordingly, it is necessary to generate a new oscillator having a phase difference appropriate for walking assistance relative to the hip joint angular velocity (walking oscillator) $\phi_H'$ on the basis of the first oscillator x.

Hence, (2) an angular velocity (a new intrinsic angular velocity) $\omega_m$ of a virtual walking assist oscillator $\theta_m$ is determined according to an "internal model" (s6.1 through s6.3 in FIG. 2). Furthermore, a second oscillator y is generated that tugs and is tugged by the hip joint angular velocity (the walking oscillator) $\phi_H'$ such that the intrinsic angular velocity $\omega_m$ is reflected, and has a second phase difference $\theta_{hm}$ which is closer to the desired phase difference $\theta_d$ than the first phase difference $\theta_{HM}$ is, with respect to the walking oscillator (s7 in FIG. 2).

Generating the second oscillator y is equivalent to correcting the intrinsic angular velocity $\omega_M$ to a new intrinsic angular velocity $\omega_M$ so as to bring the first phase difference $\theta_{HM}$ closer to the desired phase difference $\theta_d$ (refer to the above expressions (1a) and (1b)), and then regenerating the first oscillator x such that the corrected intrinsic angular velocity $\omega_m$ is reflected (refer to the above expressions (7a) and (7b)).

The rhythm of the second oscillator y thus generated has the desired phase difference $\theta_d$ or a phase difference close thereto (~a second phase difference $\theta_{hm}$) with respect to a walking rhythm (~rhythm of the walking oscillator $\phi_H'$). Thus, if the torque (the walking assist oscillator) T is determined on the basis of the second oscillator y, then the phase difference between the walking rhythm and the walking assist rhythm approaches to the desired phase difference $\theta_d$.

Thus, (3) an output (neural oscillator) $z_i$ of the neural element i is generated according to the "neural element model" on the basis of the second oscillator y and the hip joint angle (the walking oscillator) $\phi_H$ (s8 in FIG. 2), and then the torque (walking assist oscillator) T is generated on the basis of each output $z_i$ (s9 in FIG. 2). This generates the torque (the walking assist oscillator) T so as to allow the walking rhythm (~the rhythm of the walking oscillator $\phi_H'$) and the desired phase difference $\theta_d$ to be achieved. Furthermore, the walk of the walker can be assisted at a rhythm based on a walking condition reflected in the walking rhythm.

Accordingly, the present invention makes it possible to achieve a walking assist rhythm that (1) follows changes in the walking rhythm (~the rhythm of the walking oscillator $\phi_H'$) of a walker, while (2) maintaining autonomy that has the walking rhythm and a desired phase difference $\theta_d$, and (3) achieving smooth walking assistance according to a walking condition of the walker.

As described above, a walking assist rhythm harmonizes with a change in a walking rhythm when the walking rhythm changes, and the walking rhythm harmonizes with the walking assist rhythm, thus allowing the walker (human body) and the walking assist device (machine) 200 to harmonize with each other (mutual concession). This arrangement makes it possible to achieve appropriate walking assistance while allowing a walker to reasonably feel that his/her walk is being assisted by the walking assist device 200. Moreover, even if a walking rhythm suddenly changes, the walking assist rhythm does not fully follow the sudden change, making it possible to avoid furthering walking assistance and walking that cause burden to the mind and body of the walker.

Moreover, the phase difference between a walking rhythm and a walking assist rhythm is brought close to the desired phase difference $\theta_d$ that changes according the walking condition of a walker (refer to arrow ④ in FIG. 2) (refer to s5, etc. in FIG. 2). This makes it possible to accomplish walking with proper walking assistance responsive to changes in the walking condition of a walker.

Furthermore, when the desired phase difference $\theta_d$ is determined to be + (refer to s5 in FIG. 2), the walking rhythm and the walking assist rhythm will have a phase difference of the determined value (>0) or a phase difference close thereto, enabling the walker to walk by leading the walking assist device 200 (walker-led walking). Conversely, when the desired phase difference $\theta_d$ is determined to be— (refer to s5 in FIG. 2), the walking rhythm and the walking assist rhythm will have a phase difference of the determined value (<0) or a phase difference close thereto, enabling the walker to walk by being led by the walking assist device 200 (walk led by the walking assist device).

Thus, the walker can walk by leading the walking assist device 200 in "a descending walk condition" wherein burden is relatively small, while by being led by the walking assist device 200 in "an ascending walk condition" wherein burden is relatively large. The desired phase difference can be changed according to walker's intention or other factors rather than being fixed to 0, + or − according to a walking condition.

Referring now to FIG. 4 through FIG. 9, the results of experiments of walk using the walking assist device 200 controlled by the control system 100 will be explained.

Figure 4:
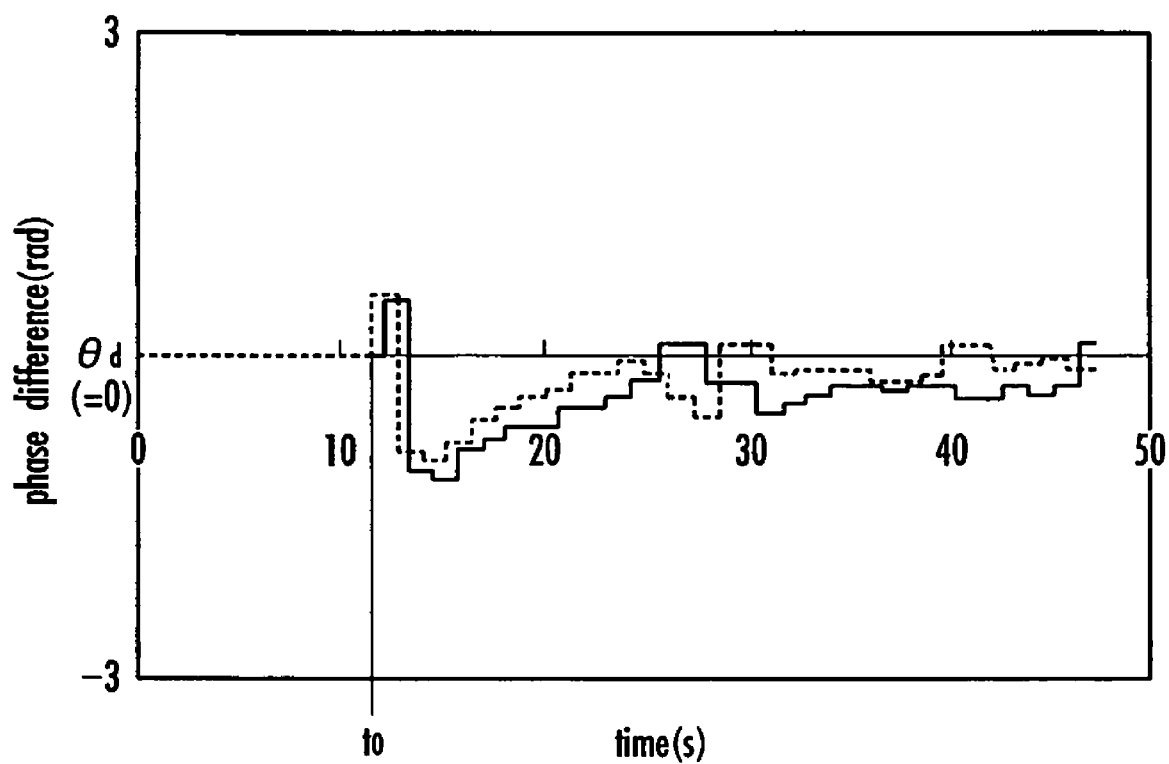
FIG. 4 is an explanatory diagram (part 1) of a walking assist function according to the embodiment of the control system in accordance with the present invention.
Figure 5:
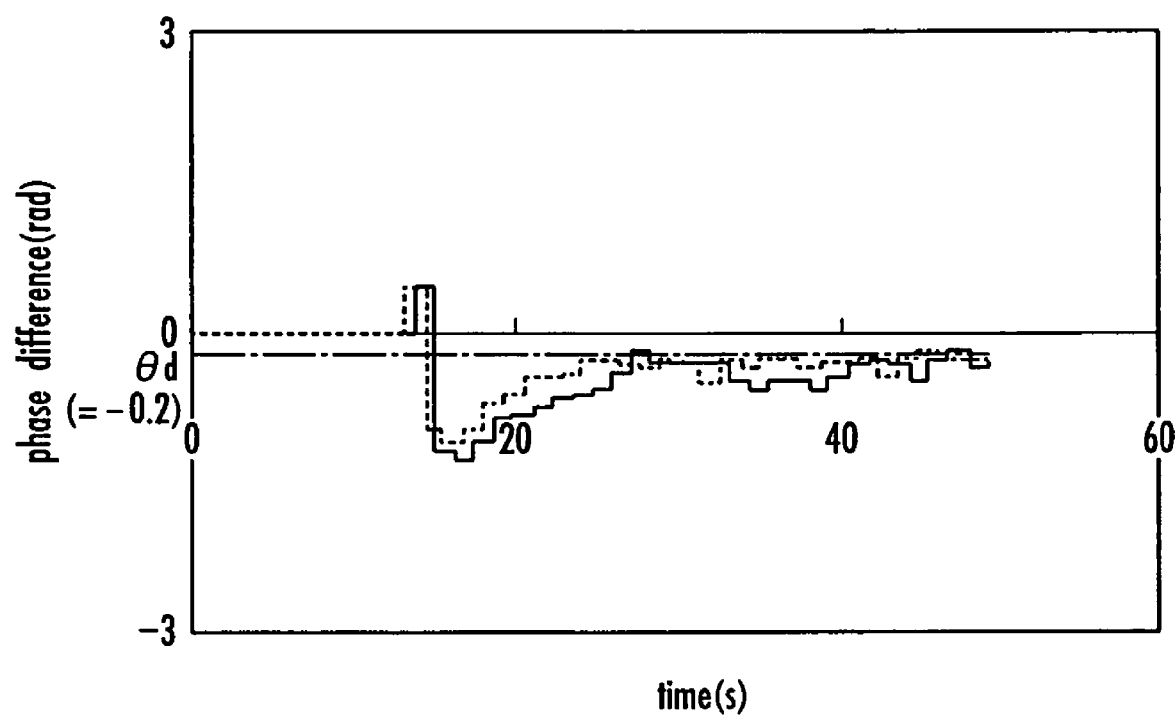
FIG. 5 is an explanatory diagram (part 2) of a walking assist function according to the embodiment of the control system in accordance with the present invention.
Figure 6:
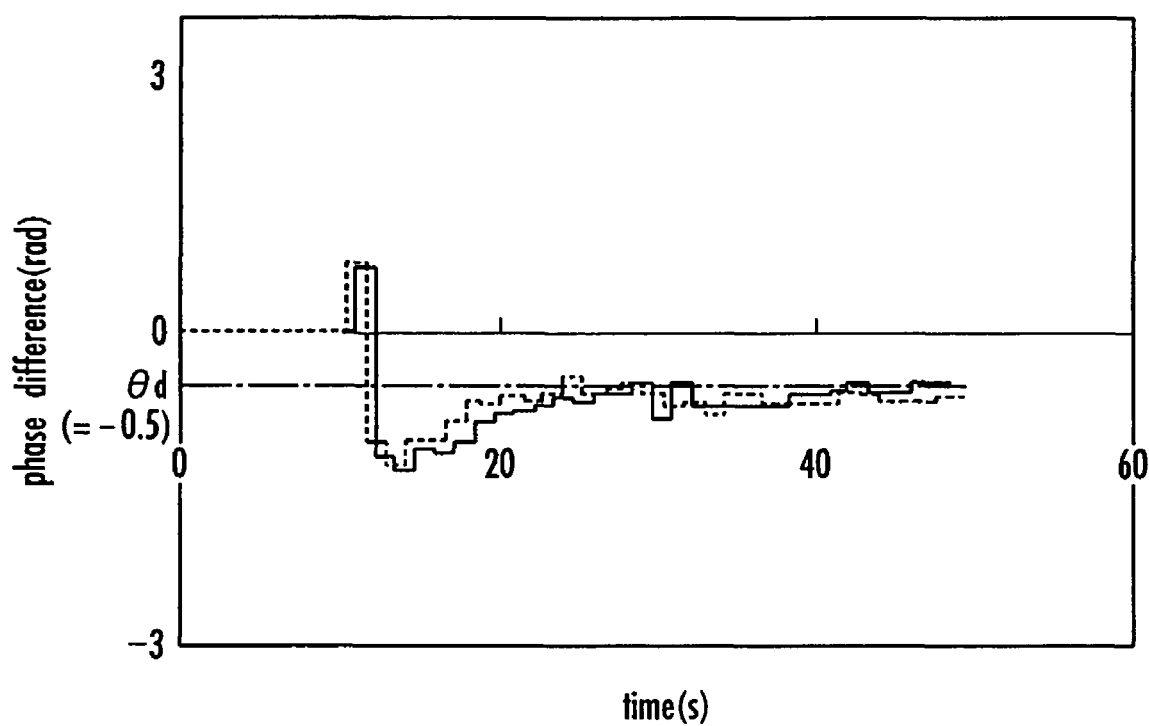
FIG. 6 is an explanatory diagram (part 3) of a walking assist function according to the embodiment of the control system in accordance with the present invention.

FIG. 4, FIG. 5, and FIG. 6 show how the phase difference between the hip joint angular velocity (walking oscillator) $\phi_H{}'$ and the torque (walking assist oscillator) T changes when the desired phase difference $\theta_d$ is set to 0.0[rad], −0.2[rad], and −0.5[rad], respectively. The solid lines indicate phase differences on the right leg, while the dashed lines indicate phase differences on the left leg.

As shown in FIG. 4 through FIG. 6, the phase differences exhibit relatively large changes immediately after time $t_0$ when walking assistance begins. Then, the phase differences gradually converge to the desired phase difference $\theta_d$ respectively set. As is obvious from the results, according to the control system 100, the phase difference between the walking rhythm (~vibration rhythm of the hip joint angular velocity $\phi_H{}'$) and the walking assist rhythm (~vibration rhythm of the torque T) can be brought close to the desired phase difference $\theta_d$ determined from the viewpoint of walking assistance with a proper rhythm.

Figure 7:
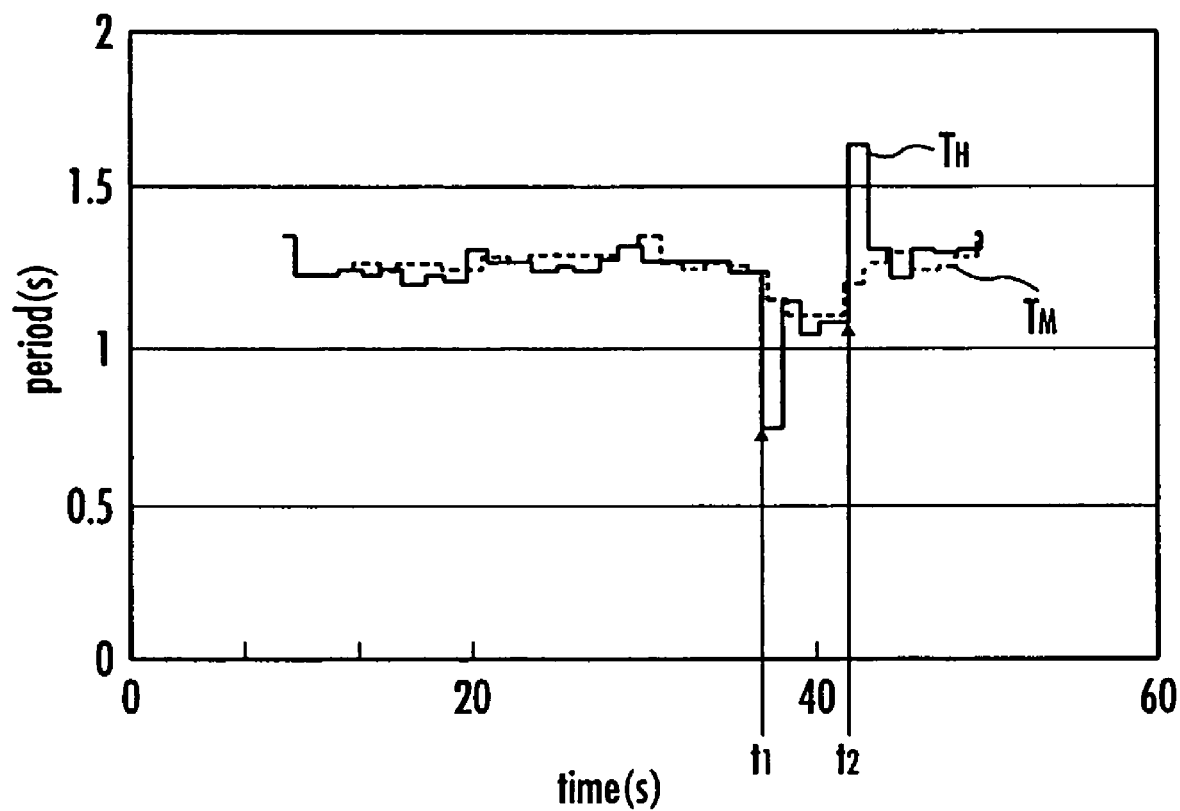
FIG. 7 is an explanatory diagram (part 4) of a walking assist function according to the embodiment of the control system in accordance with the present invention.
Figure 8:
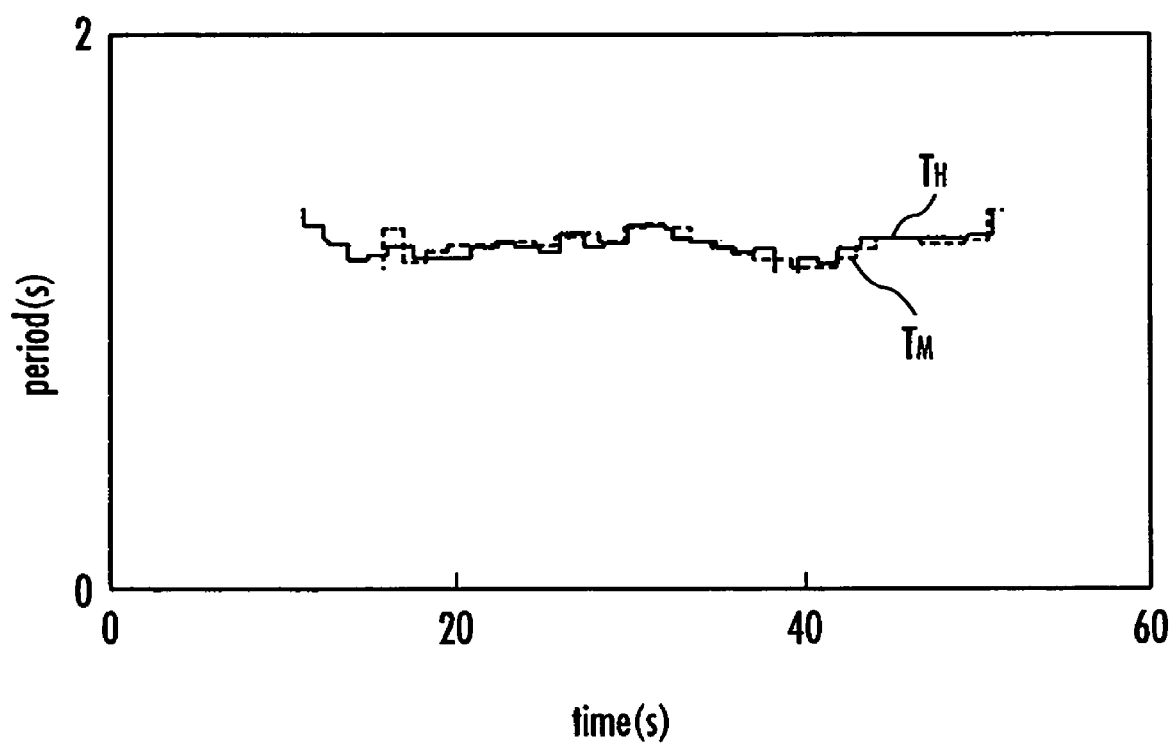
FIG. 8 is an explanatory diagram (part 5) of a walking assist function according to the embodiment of the control system in accordance with the present invention.

FIG. 7 and FIG. 8 show changes in walking period $T_H$ (solid lines) and walking assist period $T_M$ (dashed lines). As shown in FIG. 7, if a walker suddenly increases the walking speed at time $t_1$, resulting in a shorter walking period $T_H$, then the walking assist period $T_M$ shortens accordingly. If the walker suddenly decreases the walking speed at time $t_2$, resulting in a longer walking period $T_H$, then the walking assist period $T_M$ is prolonged accordingly. It is understood, however, that the walking assist period $T_M$ does not completely follow the walking period $T_H$. Instead, the walking assist period $T_M$ is slightly changed, and the walking period $T_H$ changes to follow $T_M$ after the change.

As is obvious from the above, the control system 100 allows a walking assist rhythm to harmonize with a change in a walking rhythm when the walking rhythm changes, and the walking rhythm harmonizes with the walking assist rhythm, thus allowing the walker (human body) and a walking assist device (machine) 200 to harmonize with each other (mutual concession). Thus, it is possible to achieve appropriate walking assistance while allowing a walker to reasonably feel that his/her walk is being assisted by the walking assist device 200. Moreover, even if a walking rhythm suddenly changes, the walking assist rhythm does not fully follow the sudden change. This arrangement is expected to allow avoidance of furthering of walking assistance and walking that cause burden to the mind and body of the walker.

The same applies to a case where the walking period $T_H$ (solid lines) slowly changes, as shown in FIG. 8, rather than changing suddenly.

Figure 9:
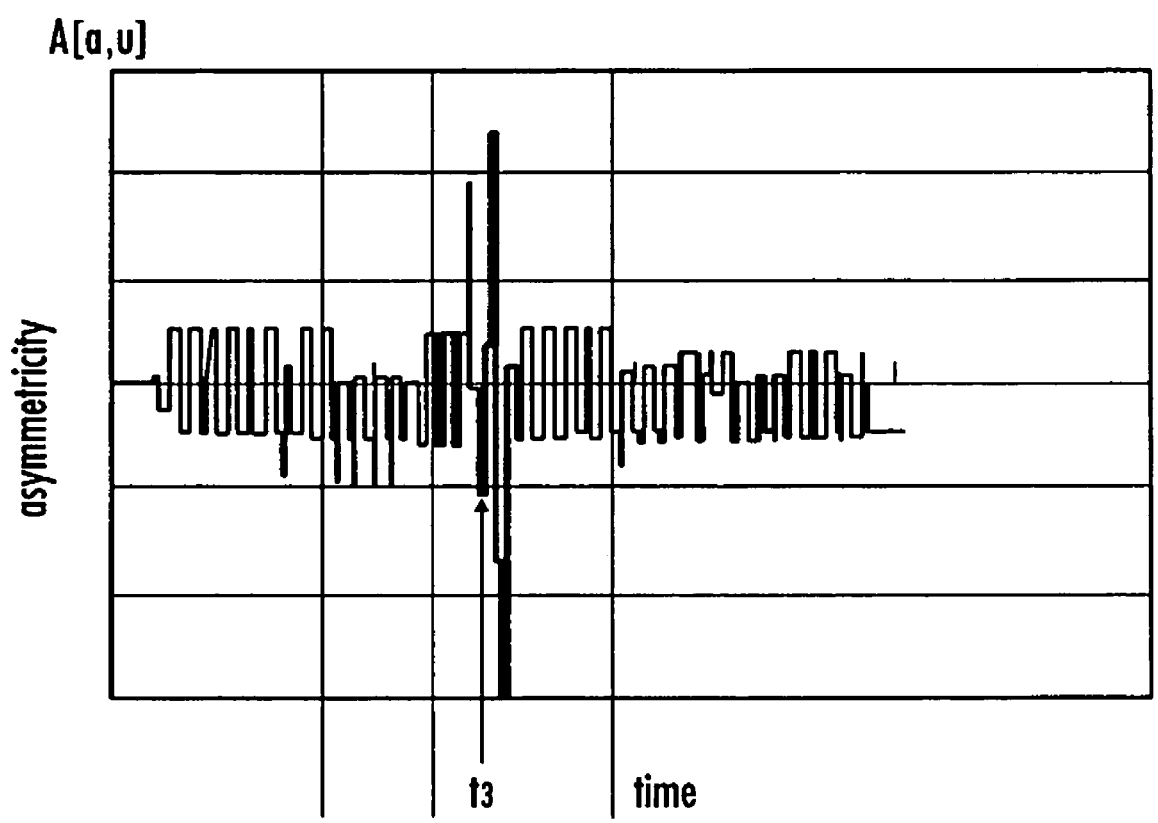
FIG. 9 is an explanatory diagram (part 6) of a walking assist function according to the embodiment of the control system in accordance with the present invention.

FIG. 9 shows how a walk symmetry parameter A indicating symmetric properties of motions of the right and left legs changes when one leg is loaded with a weight (~11 kg), the control of the walking assist device 200 by the control system 100 is intermittently turned ON/OFF, and a walker makes a U turn at time $t_3$. The walk symmetry parameter A is represented by a difference between the landing period of one leg and the landing period of the other leg. The walk symmetry parameter A approaches to zero when both legs are moving with equivalent landing periods, whereas it shifts away from zero if a difference is developed between the landing periods of the two legs, as in a case where one leg is dragged or the like.

As is obvious from FIG. 9, while the control of the walking assist device 200 by the control system 100 is ON, an absolute value of the walk symmetry parameter A is smaller, as a whole, than while the control is OFF. This indicates that the landing rhythms of the two legs are harmonized by the control system 100, whereas the one leg loaded with the weight would be dragged when the walker walks, resulting in an increased difference between the landing periods of the two legs.

The landing rhythms of the two legs are harmonized, as described above, because terms including correlation factors g of the right and left legs are included in the Van der Pol equations of the above expressions (1a), (1b), (7a), and (7b). More specifically, the first oscillators $x_L$ and $x_R$ associated with virtual left and right motions tug with each other, and similarly, the second oscillators $y_L$ and $y_R$ associated with virtual left and right motions tug with each other. Hence, even if only one leg is loaded (due to an injury or the like), adjusting the correlation factors g makes it possible to further reduce the absolute value of the walk symmetry parameter A and to achieve walking similar to normal walking with the same landing rhythms for both right and left legs.

In the present embodiment, the torque T has been imparted about hip joints after the hip joint angle $\phi_H$ and the angular velocity $\phi_H{}'$ are measured. As another embodiment, however, a torque may be imparted about knee joints after a knee joint angle and angular velocity are measured, or a torque may be imparted about a foot joint after a foot joint angle and angular velocity are measured.

Figure 10:
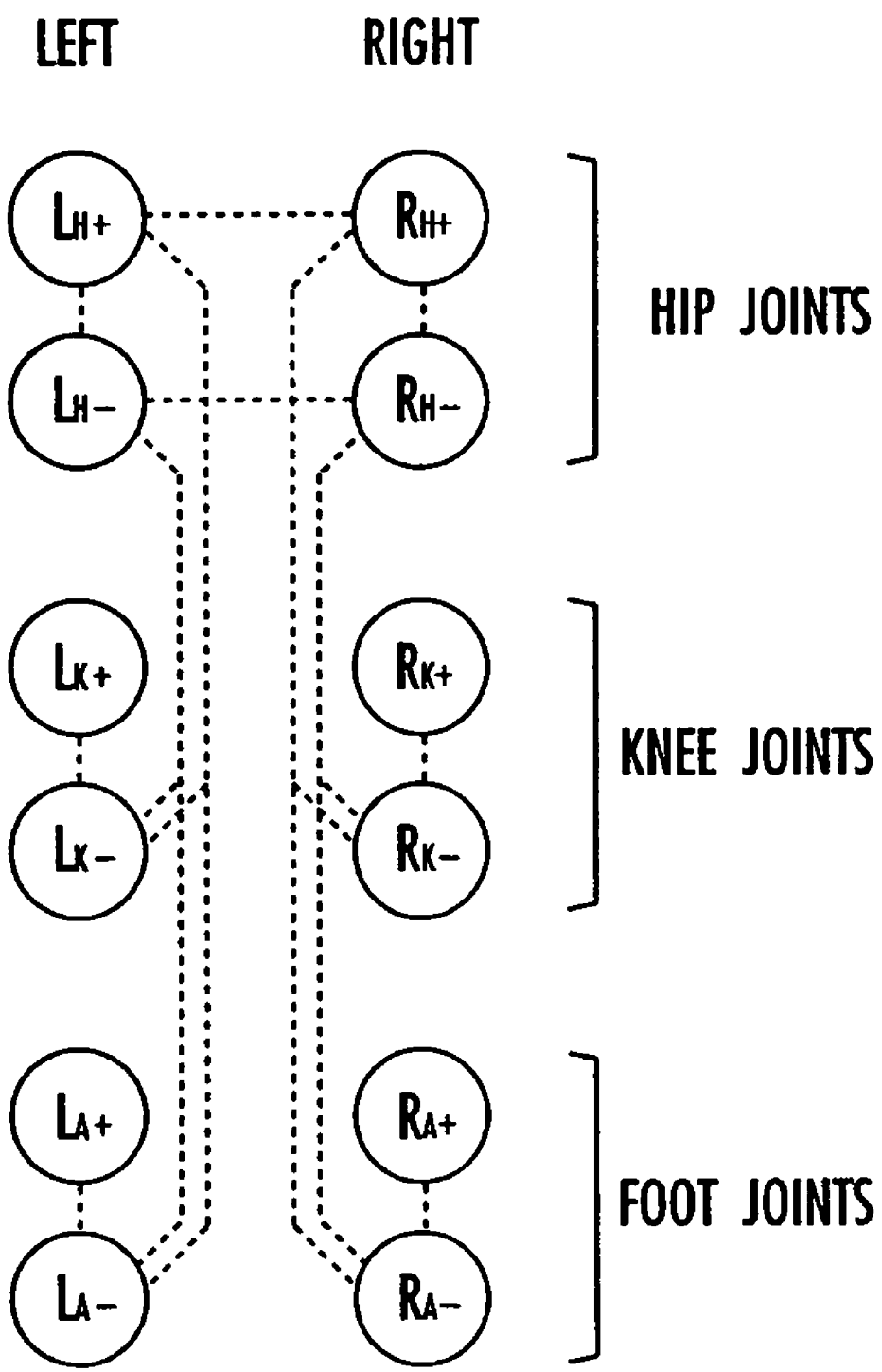
FIG. 10 is an explanatory diagram of a neural oscillator model of another embodiment of the control system in accordance with the present invention.

In the present embodiment, the torques about a pair of joints have been imparted to the walker. However, as another embodiment, torques about a plurality of pairs of joints (the right and left hips+knee joints, the right and left hips+foot joints, the right and left knees+foot joints, and the right and left hips+knees+foot joints) may be imparted to a walker. For instance, if torques are to be imparted about all joints (hip+knee+foot joints) of the right and left legs, then the torque to be imparted about each joint may be determined according to a neural oscillator model representing the behaviors of neural elements of a plurality of pairs related to stretching and bending for each joint, which interact with each other, as shown in FIG. 10.

As the number of walking oscillators to be measured increases, the number of correlation terms in the nonlinear differential equations (refer to the above expressions (1a), (1b), (7a), and (7b)) related to the generation of the first and second oscillators x and y of the Van der Pol equations or the like, and in the nonlinear differential equations (refer to the above expressions (8a) through (8f)) related to the generation of neural oscillators increases. Nevertheless, more accurate walking assistance based on the motions of diverse parts of the body of a walker can be achieved by adjusting the correlation factors.

In the present embodiment, the first oscillators x and the second oscillators y have been generated according to the Van der Pol equations represented by the equations (1a), (1b), (7a), and (7b). As another embodiment, however, the first oscillators x and the second oscillators y may be generated according Van der Pol equations of a form different from the above expressions, or according to any forms of nonlinear differential equations that permit mutual tugging among a plurality of oscillators.

In the present embodiment, the hip joint angular velocity $\phi_H'$ has been measured as the "walking oscillator" related to the generation of the first and second oscillators x and y (refer to arrows ①-1 and ①-4 in FIG. 2). As another embodiment, however, various parameters, such as the hip joint angle $\phi_H$, or the angles or angular velocities of knee joins, foot joints, shoulder joints or elbow joints, or a landing noise, breath sound, or intended utterance of the walker, which vary with a rhythm associated with a walking rhythm may be measured as the "walking oscillators" related to the generation of the first and second oscillators x and y.

In the present embodiment, the hip joint angle $\phi_H$ has been measured as the "walking oscillator" related to the generation of the torque (walking assist oscillator) T (refer to arrow ⑥ in FIG. 2). As another embodiment, however, various parameters, such as the hip joint angular velocity $\phi_H'$, or the angles or angular velocities of knee joins, foot joints, shoulder joints or elbow joints, or a landing noise, breath sound, or intended utterance of the walker, which vary with a rhythm associated with a walking rhythm may be measured as the "walking oscillators" related to the generation of the torque T.

In the present embodiment, the torques T about joints to be imparted to a walker through the actuators 210 have been generated as the "walking assist oscillators" (refer to s8 in FIG. 2). In another embodiment, the torques T as the "walking assist oscillators" may be replaced by, for example, periodic sounds that can be acoustically perceived by a walker through an audio device, such as a headphone (not shown), periodic light or a sign that can be perceived through a visual device (not shown), such as goggles, or periodic tapping (knocking) that can be perceived, via a device or the like, by a walker in terms of sensation at a part of his/her body, such as the back or shoulder.

In the present embodiment, walking conditions have been determined on the basis of the walking oscillators measured by the walking oscillator measuring unit 110. As another embodiment, physiological parameters representing a physiological condition of a walker (e.g., the potentials of muscles that move when the walker walks) may be measured by a physiological parameter measuring unit (not shown), and then a "walking condition" may be determined by the walking condition determining unit 140 on the basis of the pattern of the physiological parameters.

In the present embodiment, a "walking condition" has been determined as "the ascending walk condition," "the flat walk condition," or "the descending walk condition." In another embodiment, as a "walking condition," the speed of walking may be determined separately or in addition to the above. In this embodiment, the desired phase difference determining unit 150 may basically determine the desired phase difference $\theta_d$ to be − (e.g., −0.2 [rad] or less) if walking is fast, or + (e.g., +0.5 [rad] or more) if walking is slow.

The present embodiment enables the walker to walk by leading the walking assist device 200 in "slow walking" wherein burden is relatively small, while by being led by the walking assist device 200 in "fast walking" wherein burden is relatively large.

If "the descending walk condition" for which the desired phase difference $\theta_d$ is basically determined to be + is combined with "the fast walking" for which the desired phase difference $\theta_d$ is basically determined to be −, then a basic desired phase difference $\theta_d$ may be determined by fuzzy control that permit these two conditions to be matched.

Another embodiment of the control system 100 in accordance with the present invention may be provided with "a first correlation adjusting unit" for adjusting the correlation factors g (refer to the above expressions (1a), (1b), (7a), and (7b)) of the right and left legs (a plurality of virtual objects) related to the generation of the first and second oscillators x and y according to the "walking condition" determined by the walking condition determining unit 140.

The present embodiment makes it possible to properly adjust a walking assist rhythm on the basis of a qualitative correlation between the right and left legs, and also to achieve walking assistance in real time at an optimum rhythm for a walking condition, taking into account the fact that the qualitative correlation changes as the walking condition changes.

Still another embodiment of the control system 100 in accordance with the present invention may be provided with "a second correlation adjusting unit" for adjusting a correlation factor $w_{i/j}$ (refer to the above expressions (8a) through (8d)) among a plurality of virtual neural elements i and j (refer to FIG. 2) related to the generation of walking assist oscillators, such as the torques T, according to the "walking condition" determined by the walking condition determining unit 140.

The present embodiment makes it possible to properly adjust a walking assist rhythm by adjusting the correlation intensity of a plurality of virtual neural elements, and also to achieve walking assistance in real time at an optimum rhythm for a walking condition, taking into account the fact that the correlation intensity changes as the walking condition changes.

Still another embodiment of the control system 100 in accordance with the present invention may be provided with a "physiological condition determining unit" for determining the "physiological condition" of a walker on the basis of a walking assist oscillator measured by the walking assist oscillator measuring unit 110, or the amounts of other conditions (e.g., the heart rate, the respiration rate, the concentration of lactic acid, oxygen, etc. of blood, the amount of perspiration, and the number of blinks of the walker). Then, the desired phase difference $\theta_d$ may be determined by the desired phase difference determining unit 150 on the basis of the "physiological condition" determined by the physiological condition determining unit.

According to the present embodiment, the phase difference between a walking rhythm and a walking assist rhythm can be brought close to the desired phase difference $\theta_d$ that varies according to the physiological condition of the walker, thus making possible to accomplish walking with proper walking assistance responsive to changes in physiological condition.

Alternatively, "the physiological condition determining unit" may determine the "fatigue" of a walker, and then "the desired phase difference determining unit" may determine the desired phase difference $\theta_d$ so that it is basically determined to be 0 for a flat physiological condition, − (e.g., −0.5[rad] or less) for an ascending physiological condition, and + (e.g., +0.3[rad] or more) for a descending physiological condition.

The present embodiment enables a walker to walk by leading the walking assist device 200 when the level of his/her fatigue is low, and to walk by being led by the walking assist device 200 when the level of his/her fatigue is high. The desired phase difference can be changed according to walker's intention or other factors rather than being fixed to + or − according to the physiological condition.

Yet another embodiment of the control system 100 in accordance with the present invention may be provided with a "physiological condition determining unit" for determining the physiological condition of the walker on the basis of a "walking assist oscillator" measured by the walking assist oscillator measuring unit 110, and "a first correlation adjusting unit" for adjusting correlation factors g (refer to the above expressions (1a), (1b), (7a), and (7b)) of the right and left legs (a plurality of virtual objects) related to the generation of the first and second oscillators x and y according to the "physiological condition" determined by the physiological condition determining unit.

The present embodiment makes it possible to properly adjust a walking assist rhythm on the basis of a qualitative correlation between the right and left legs, and also to achieve walking assistance in real time at an optimum rhythm for a physiological condition, taking into account the circumstance that the qualitative correlation changes as the physiological condition changes.

Still another embodiment of the control system 100 in accordance with the present invention may be provided with "a physiological condition determining unit" for determining a "physiological condition" of a walker on the basis of "walking assist oscillators" measured by the walking assist oscillator measuring unit 110, and "a second correlation adjusting unit" for adjusting a correlation factor $w_{i/j}$ (refer to the above expressions (8a) through (8d)) among a plurality of virtual neural elements i and j (refer to FIG. 2) related to the generation of walking assist oscillators according to the "physiological condition" determined by the physiological condition determining unit.

The present embodiment makes it possible to properly adjust a walking assist rhythm by adjusting the correlation intensity of a plurality of virtual neural elements, and also to achieve walking assistance in real time at an optimum rhythm based on physiological conditions, taking into account the circumstance that the correlation intensity changes as the physiological condition changes.

Another embodiment of the control system 100 in accordance with the present invention may adopt the following construction. First, the functions of the determining unit 160 and the second oscillator generating unit 170 are temporarily suspended. Then, the first oscillator x is directly supplied to the neural oscillator generating unit 180 (directly proceeding from arrow ② to arrow ⑦ in FIG. 2), and the neural oscillator z and the torque T are determined (s8 and s9 in FIG. 2). Subsequently, a third phase difference determining unit (not shown) measures the phase difference between the hip joint angular velocity (walking oscillator) $\phi_H{'}$ and the torque (walking assist oscillator) T. Further, the desired phase difference determining unit 150 determines the desired phase difference $\theta_d$ that is identical or close to the aforesaid phase difference. Then, the functions of the determining unit 160 and the second oscillator generating unit 170 are restored, and the second oscillator y is generated (refer to s6.1 through s6,3 and s7 in FIG. 2) on the basis of the latest desired phase difference $\theta_d$ (refer to arrow ⑤ in FIG. 2). Lastly, the neural oscillator z and the torque T are generated (refer to s8 and s9 in FIG. 2) on the basis of the second oscillator y (refer to arrow ⑦ in FIG. 2).

According to the present embodiment, temporarily suspending the functions of the determining unit 160 and the second oscillator generating unit 170 generally causes the phase difference between the hip joint angular velocity (walking oscillator) $\phi_H{'}$ and the torque (walking assist oscillator) T to move away from the desired phase difference $\theta_d$ up to that moment. In addition, the phase difference converges to an optimum phase difference based on the harmony between a walker and the walking assist device 200. Thereafter, a new desired phase difference $\theta_d$ is determined that is identical or close to the aforesaid phase difference, and then the functions of the determining unit 160 and the second oscillator generating unit 170 are restored to control the torque (walking assist oscillator) T so as to bring the walk and the walking assistance close to the new desired phase difference $\theta_d$.

As described above, the new desired phase difference $\theta_d$ is an optimum phase difference (or a phase difference approximate thereto) from the viewpoint of harmony between a walker and the walking assist device 200. This enables the walker to walk with a rhythm optimally matched with a walking assist rhythm by the walking assistance provided by the walking assist device 200.

The invention claimed is:

1. A control system comprising:

walking oscillator measuring means for measuring a walking oscillator of a walker whose walk is assisted by a walking assist device;

first oscillator generating means for generating a first oscillator that tugs and is tugged by a walking oscillator measured by the walking oscillator measuring means such that an intrinsic angular velocity is reflected;

determining means for determining a new intrinsic angular velocity on the basis of a difference between a first phase difference between the first oscillator and the walking oscillator and a desired phase difference;

second oscillator generating means for generating a second oscillator that tugs and is tugged by a walking oscillator measured by the walking oscillator measuring means such that the intrinsic angular velocity determined by the determining means is reflected, and has a second phase difference, which is closer to the desired phase difference than the first phase difference is, with respect to the walking oscillator; and walking assist oscillator generating means for generating a walking assist oscillator of the walking assist device on the basis of the second oscillator and the walking oscillator measured by the walking oscillator measuring means.

2. The control system according to claim 1, comprising: walking condition determining means for determining the walking condition of the walker on the basis of a walking oscillator measured by the walking oscillator measuring means; and desired phase difference determining means for determining a desired phase difference on the basis of the walking condition of the walker determined by the walking condition determining means.

3. The control system according to claim 1, comprising: physiological parameter measuring means for measuring physiological parameters indicating a physiological condition of a walker; walking condition determining means for determining a walking condition of the walker on the basis of the physiological parameters measured by the physiological parameter measuring means, and desired phase difference determining means for determining a desired phase difference on the basis of a walking condition of the walker determined by the walking condition determining means.

4. The control system according to claim 2, wherein the walking condition determining means determines whether a walking condition of a walker is a flat walk condition, an ascending walk condition, or a descending walk condition, and
the desired phase difference determining means basically determines a desired phase difference to be 0 for the flat walk condition, − for the ascending walk condition, and + for the descending walk condition.

5. The control system according to claim 2, wherein the walking condition determining means determines the speed of walk as a walking condition, and
the desired phase difference determining means basically determines a desired phase difference to be − if the walk is fast, or + if the walk is slow.

6. The control system according to claim 1, comprising: physiological parameter measuring means for measuring physiological parameters indicating a physiological condition of a walker; a physiological condition determining means for determining a physiological condition of the walker on the basis of the physiological parameters measured by the physiological parameter measuring means; and
desired phase difference determining means for determining a desired phase difference on the basis of a physiological condition of the walker determined by the physiological condition determining means.

7. The control system according to claim 6, wherein the physiological condition determining means determines fatigue of a walker as a physiological condition of the walker, and basically determines a desired phase difference to be + if the fatigue of the walker is small, or − if the fatigue of the walker is large.

8. The control system according to claim 1, wherein the first oscillator generating means generates a plurality of first oscillators corresponding to the motions of a plurality of objects such that correlation among a plurality of virtual objects is reflected, and
the second oscillator generating means generates a plurality of second oscillators corresponding to the motions of the plurality of the objects such that correlation among a plurality of virtual objects is reflected.

9. The control system according to claim 8, comprising: walking condition determining means for determining a walking condition of a walker on the basis of a walking oscillator measured by a walking oscillator measuring means; and
first correlation adjusting means for adjusting a correlation among a plurality of virtual objects related to generation of first and second oscillators on the basis of a walking condition of the walker determined by the walking condition determining means.

10. The control system according to claim 8, comprising: physiological parameter measuring means for measuring physiological parameters indicating a physiological condition of a walker; walking condition determining means for determining a walking condition of the walker on the basis of the physiological parameters measured by the physiological parameter measuring means; and
first correlation adjusting means for adjusting a correlation among a plurality of virtual objects related to the generation of the first and second oscillators on the basis of the walking condition of the walker determined by the walking condition determining means.

11. The control system according to claim 8, comprising: physiological parameter measuring means for measuring physiological parameters indicating a physiological condition of a walker, a physiological condition determining means for determining the physiological condition of the walker on the basis of the physiological parameters measured by the physiological parameter measuring means; and
first correlation adjusting means for adjusting a correlation among a plurality of virtual objects related to the generation of the first and second oscillators on the basis of the physiological condition of the walker determined by the physiological condition determining means.

12. The control system according to claim 1, wherein determining means determines an intrinsic angular velocity for bringing a second phase difference between a second oscillator and a walking oscillator closer to a desired phase difference than a first phase difference between a first oscillator and a walking oscillator according to an internal model representing a phase relationship between a virtual walking oscillator and a virtual walking assist oscillator.

13. The control system according to claim 12, wherein the determining means comprises:
correlation factor determining means for determining correlation factors of a virtual walking oscillator and a virtual walking assist oscillator such that the second phase difference of the virtual walking oscillator and the virtual walking assist oscillator approaches to the first phase difference according to the internal model;
first angular velocity determining means for determining an angular velocity of the virtual walking oscillator on the basis of the correlation factors; and
second angular velocity determining means for determining an angular velocity of the virtual walking assist oscillator as an intrinsic angular velocity related to the generation of the second oscillator such that the second phase difference approaches to a desired phase difference on the basis of the angular velocity of the virtual walking oscillator.

14. The control system according to claim 1, wherein the walking assist oscillator generating means generates walking assist oscillators corresponding to behaviors of a plurality of neural elements such that a correlation among the plurality of virtual neural elements is reflected.

15. The control system according to claim 14, comprising:
walking condition determining means for determining a walking condition of a walker on the basis of a walking oscillator measured by a walking oscillator measuring means; and
second correlation adjusting means for adjusting a correlation among a plurality of virtual neural elements related to the generation of a walking assist oscillator on the basis of the walking condition of the walker determined by the walking condition determining means.

16. The control system according to claim 14, comprising:
physiological parameter measuring means for measuring physiological parameters indicating a physiological condition of a walker; walking condition determining means for determining the walking condition of the walker on the basis of the physiological parameters measured by the physiological parameter measuring means; and
second correlation adjusting means for adjusting a correlation among a plurality of virtual neural elements related to the generation of the a walking assist oscillator on the basis of the walking condition of the walker determined by the walking condition determining means.

17. The control system according to claim 14, comprising:
physiological parameter measuring means for measuring physiological parameters indicating a physiological condition of a walker; physiological condition determining means for determining the physiological condition of the walker on the basis of the physiological parameters measured by the physiological parameter measuring means; and
second correlation adjusting means for adjusting a correlation among a plurality of virtual neural elements related to the generation of the walking assist oscillator on the basis of the walking condition of the walker determined by the walking condition determining means.

18. The control system according to claim 2, comprising:
storing means for storing a correspondence relationship between a walking condition and a tracing pattern drawn by an n number of walking oscillators in an n-dimensional space, wherein the walking condition determining means determines a walking condition on the basis of the correspondence relationship stored by the storing means and the tracing pattern drawn in the n-dimensional space by the n number of walking oscillators measured by the walking oscillator measuring means.

19. The control system according to claim 1, wherein the first and second oscillator generating means generate the first and second oscillators according to a nonlinear oscillator model represented by the Van der Pol equation that includes a walking oscillator measured by the walking oscillator measuring means.

20. The control system according to claim 1, wherein the walking oscillator measuring means measures the first oscillator, the second oscillator, and at least one of various oscillators including a joint angle and angular velocity of a walker that periodically changes at a rhythm corresponding to a walking rhythm, as a walking oscillator for generating a walking assist oscillator.

21. The control system according to claim 1, wherein the walking assist oscillator generating means generates, as a walking assist oscillator, a torque about a leg joint imparted to a walker, or a oscillator that periodically changes in a form perceivable by a walker in response to a torque and a change in torque.

22. The control system according to claim 2 wherein the walking oscillator measuring means measures, as a walking oscillator for determining a walking condition, at least one of a leg joint angle, a leg joint angular velocity, a leg joint angular acceleration, and the position of a part of a leg of a walker.

23. The control system according to claim 3, wherein
the walking condition determining means determines whether a walking condition of a walker is a flat walk condition, an ascending walk condition, or a descending walk condition, and
the desired phase difference determining means basically determines a desired phase difference to be 0 for the flat walk condition, − for the ascending walk condition, and + for the descending walk condition.

24. The control system according to claim 3, wherein
the walking condition determining means determines the speed of walk as a walking condition, and
the desired phase difference determining means basically determines a desired phase difference to be − if the walk is fast, or + if the walk is slow.

25. The control system according to claim 9, comprising:
storing means for storing a correspondence relationship between a walking condition and a tracing pattern drawn by an n number of walking oscillators in an n-dimensional space, wherein the walking condition determining means determines a walking condition on the basis of the correspondence relationship stored by the storing means and the tracing pattern drawn in the n-dimensional space by the n number of walking oscillators measured by the walking oscillator measuring means.

26. The control system according to claim 15, comprising:
storing means for storing a correspondence relationship between a walking condition and a tracing pattern drawn by an n number of walking oscillators in an n-dimensional space, wherein the walking condition determining means determines a walking condition on the basis of the correspondence relationship stored by the storing means and the tracing pattern drawn in the n-dimensional space by the n number of walking oscillators measured by the walking oscillator measuring means.

27. The control system according to claim 9, wherein the walking oscillator measuring means measures, as a walking oscillator for determining a walking condition, at least one of a leg joint angle, a leg joint angular velocity, a leg joint angular acceleration, and the position of a part of a leg of a walker.

28. The control system according to claim 15, wherein the walking oscillator measuring means measures, as a walking oscillator for determining a walking condition, at least one of a leg joint angle, a leg joint angular velocity, a leg joint angular acceleration, and the position of a part of a leg of a walker.

29. The control system according to claim 18, wherein the walking oscillator measuring means measures, as a walking oscillator for determining a walking condition, at least one of a leg joint angle, a leg joint angular velocity, a leg joint angular acceleration, and the position of a part of a leg of a walker.

* * * * *